United States Patent
Stafford et al.

(10) Patent No.: US 9,743,862 B2
(45) Date of Patent: Aug. 29, 2017

(54) SYSTEMS AND METHODS FOR TRANSCUTANEOUSLY IMPLANTING MEDICAL DEVICES

(75) Inventors: Gary Ashley Stafford, Hayward, CA (US); Benjamin Mark Rush, Oakland, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 1042 days.

(21) Appl. No.: 13/434,804

(22) Filed: Mar. 29, 2012

(65) Prior Publication Data

US 2012/0253145 A1  Oct. 4, 2012

Related U.S. Application Data

(60) Provisional application No. 61/470,454, filed on Mar. 31, 2011.

(51) Int. Cl.
| | |
|---|---|
| A61B 5/1455 | (2006.01) |
| A61B 5/145 | (2006.01) |
| A61B 5/00 | (2006.01) |
| A61B 5/1473 | (2006.01) |

(52) U.S. Cl.
CPC ........ *A61B 5/14503* (2013.01); *A61B 5/6849* (2013.01); *A61B 5/1473* (2013.01); *A61B 5/14532* (2013.01); *A61B 5/14546* (2013.01); *A61B 2560/063* (2013.01)

(58) Field of Classification Search
None
See application file for complete search history.

(56) References Cited

U.S. PATENT DOCUMENTS

| | | |
|---|---|---|
| 3,123,790 A | 3/1964 | Tyler |
| 3,260,656 A | 7/1966 | Ross, Jr. |
| 3,581,062 A | 5/1971 | Aston |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |

(Continued)

FOREIGN PATENT DOCUMENTS

| | | |
|---|---|---|
| CA | 2291105 | 12/1998 |
| DE | 4401400 | 7/1995 |

(Continued)

OTHER PUBLICATIONS

Alcock, S. J., et al., "Continuous Analyte Monitoring to Aid Clinical Practice", *IEEE Engineering in Medicine and Biology Magazine*, 1994, pp. 319-325.

(Continued)

*Primary Examiner* — Eric Winakur
*Assistant Examiner* — Marjan Fardanesh
(74) *Attorney, Agent, or Firm* — One LLP

(57) ABSTRACT

Systems and methods for transcutaneously implanting medical devices, such as in vivo analyte sensors, are provided. The systems and methods involve the use of introducers or inserters made of shape memory alloy (SMA) materials which are transitionable from one operative state or configuration to another operative state or configuration, wherein the transition from state to state enables the transcutaneous implantation and/or transcutaneous explantation of the medical device.

20 Claims, 4 Drawing Sheets

(56) References Cited

U.S. PATENT DOCUMENTS

| | | |
|---|---|---|
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,622,966 A * | 11/1986 | Beard ............ 606/28 |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,665,906 A | 5/1987 | Jervis |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |

(56) References Cited

U.S. PATENT DOCUMENTS

| | | |
|---|---|---|
| 4,995,402 A | 2/1991 | Smith et al. |
| 5,000,180 A | 3/1991 | Kuypers et al. |
| 5,002,054 A | 3/1991 | Ash et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,067,957 A | 11/1991 | Jervis |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,190,546 A | 3/1993 | Jervis |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,533,977 A | 7/1996 | Matcalf et al. |
| 5,545,191 A | 8/1996 | Mann et al. |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,597,378 A | 1/1997 | Jervis |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |

(56) References Cited

U.S. PATENT DOCUMENTS

| | | |
|---|---|---|
| 5,842,983 A | 12/1998 | Abel et al. |
| 5,851,197 A | 12/1998 | Marano et al. |
| 5,865,804 A | 2/1999 | Bachynsky |
| 5,885,211 A | 3/1999 | Eppstein et al. |
| 5,899,855 A | 5/1999 | Brown |
| 5,924,979 A | 7/1999 | Sedlow et al. |
| 5,925,021 A | 7/1999 | Castellano et al. |
| 5,948,006 A | 9/1999 | Mann |
| 5,951,521 A | 9/1999 | Mastrototaro et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,995,860 A | 11/1999 | Sun et al. |
| 6,001,067 A | 12/1999 | Shults et al. |
| 6,004,278 A | 12/1999 | Botich et al. |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,302,866 B1 | 10/2001 | Marggi |
| 6,306,104 B1 | 10/2001 | Cunningham et al. |
| 6,306,141 B1 | 10/2001 | Jervis |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,437,679 B1 | 8/2002 | Roques |
| 6,440,068 B1 | 8/2002 | Brown et al. |
| 6,451,025 B1 | 9/2002 | Jervis |
| 6,478,736 B1 | 11/2002 | Mault |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,551,494 B1 | 4/2003 | Feldman et al. |
| 6,551,496 B1 | 4/2003 | Moles et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,290 B1 | 1/2004 | Lu |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |

(56) References Cited

U.S. PATENT DOCUMENTS

| | | |
|---|---|---|
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,822,454 B1 | 10/2010 | Alden et al. |
| 7,842,046 B1 * | 11/2010 | Nakao ............... A61B 17/0469 606/144 |
| 7,985,222 B2 | 7/2011 | Gall et al. |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0198444 A1 | 12/2002 | Uchigaki et al. |
| 2002/0198543 A1 * | 12/2002 | Burdulis et al. ............ 606/144 |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0116866 A1 | 6/2004 | Gorman et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |

(56) References Cited

U.S. PATENT DOCUMENTS

| | | |
|---|---|---|
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0149066 A1* | 7/2005 | Stafford .................. 606/144 |
| 2005/0154410 A1 | 7/2005 | Conway et al. |
| 2005/0165404 A1 | 7/2005 | Miller |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0267327 A1 | 12/2005 | Iizuka et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0095661 A1 | 5/2007 | Wang et al. |
| 2007/0106135 A1 | 5/2007 | Sloan et al. |
| 2007/0110124 A1 | 5/2007 | Shiraki et al. |
| 2007/0123819 A1 | 5/2007 | Mernoe et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021543 A1* | 1/2008 | Shrivastava ................ 623/1.31 |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0154286 A1 | 6/2008 | Abbott et al. |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262330 A1 | 10/2008 | Reynolds et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |

(56) References Cited

U.S. PATENT DOCUMENTS

| | | |
|---|---|---|
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0004597 A1 | 1/2010 | Gyrn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0198035 A1 | 8/2010 | Kamath et al. |
| 2010/0198036 A1 | 8/2010 | Kamath et al. |
| 2010/0204653 A1 | 8/2010 | Gyrn et al. |
| 2010/0212583 A1 | 8/2010 | Brister et al. |
| 2010/0214104 A1 | 8/2010 | Goode et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode et al. |
| 2010/0240976 A1 | 9/2010 | Goode et al. |
| 2010/0261987 A1 | 10/2010 | Kamath et al. |
| 2010/0262183 A1 | 10/2010 | Abbott et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |

(56) References Cited

U.S. PATENT DOCUMENTS

| | | |
|---|---|---|
| 2010/0331642 A1 | 12/2010 | Bruce et al. |
| 2010/0331644 A1 | 12/2010 | Neale et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0288574 A1 | 11/2011 | Curry et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2016/0354555 A1* | 12/2016 | Gibson et al. .......... A61M 5/40 |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| JP | 2004-520898 | 7/2004 |
| WO | WO-96/39977 | 5/1996 |
| WO | WO-96/25089 | 8/1996 |
| WO | WO-96/35370 | 11/1996 |
| WO | WO-97/21457 | 6/1997 |
| WO | WO-98/35053 | 8/1998 |
| WO | WO-98/56293 | 12/1998 |
| WO | WO-99/33504 | 7/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/50534 | 6/2002 |
| WO | WO-02/058537 | 8/2002 |
| WO | WO-03/028784 | 4/2003 |
| WO | WO-03/076893 | 9/2003 |
| WO | WO-03/082091 | 10/2003 |
| WO | WO-2004/060436 | 7/2004 |
| WO | WO-2004/061420 | 7/2004 |
| WO | WO-2005/084534 | 9/2005 |
| WO | WO-2005/089103 | 9/2005 |
| WO | WO-2006/042811 | 4/2006 |
| WO | WO-2006/108809 | 10/2006 |
| WO | WO-2008/065646 | 6/2008 |
| WO | WO-2008/133702 | 11/2008 |
| WO | WO-2009/062675 | 5/2009 |
| WO | WO-2010/112521 | 10/2010 |
| WO | WO-2011/002815 | 1/2011 |

OTHER PUBLICATIONS

Armour, J. C., et al., "Application of Chronic Intravascular Blood Glucose Sensor in Dogs", *Diabetes*, vol. 39, 1990, pp. 1519-1526.

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1071.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Mediated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology Results from a 3-Day Trial in Patients with

(56) References Cited

OTHER PUBLICATIONS

Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Heller, A., "Electrical Connection Enzyme Redox Centers to Electrodes", *Journal of Physical Chemistry*, vol. 96, No. 9, 1990, pp. 3579-3587.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", Smart Computing Learning Series, *Wireless Computing*, vol. 8, Issue 5, 2002, pp. 72-74.
Maidan, R., et al., "Elimination of Electrooxidizable Interferant-Produced Currents in Amperometric Biosensors", *Analytical Chemistry*, vol. 64, No. 23, 1992, pp. 2889-2896.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
Mastrototaro, J. J., et al., "An Electroenzymatic Glucose Sensor Fabricated on a Flexible Substrate", *Sensors and Actuators B*, vol. 5, 1991, pp. 139-144.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Ohara, T. J., et al., "Glucose Electrodes Based on Cross-Linked [Os(bpy)$_2$Cl]$^{+/2+}$ Complexed Poly(1-Vinylimidazole) Films", *Analytical Chemistry*, vol. 65, No. 23, 1993, pp. 3512-3517.
Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Poitout, V., et al., "In Vitro and In Vivo Evaluation in Dogs of a Miniaturized Glucose Sensor", *ASAIO Transactions*, vol. 37, No. 3, 1991, pp. M298-M300.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Reach, G., et al., "Can Continuous Glucose Monitoring Be Used for the Treatment of Diabetes?", *Analytical Chemistry*, vol. 64, No. 6, 1992, pp. 381-386.
Rebrin, K., et al., "Automated Feedback Control of Subcutaneous Glucose Concentration in Diabetic Dogs", *Diabetologia*, vol. 32, 1989, pp. 573-576.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidt, F. J., et al., "Calibration of a Wearable Glucose Sensor", *The International Journal of Artificial Organs*, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.

(56) References Cited

OTHER PUBLICATIONS

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

Ye, L., et al., "High Current Density 'Wired' Quinoprotein Glucose Dehydrogenase Electrode", *Analytical Chemistry*, vol. 65, No. 3, 1993, pp. 238-241.

\* cited by examiner

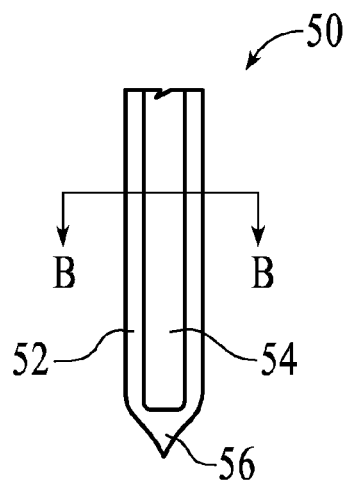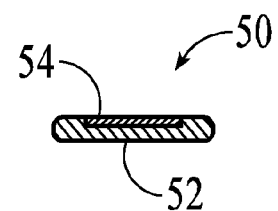
FIG. 4A     FIG. 4B
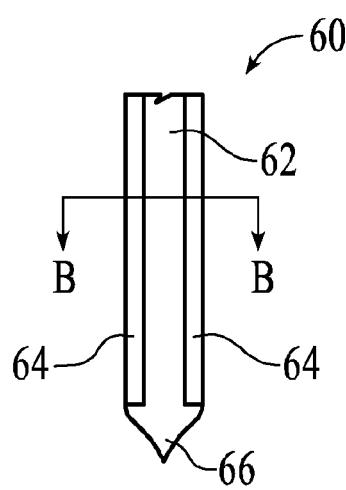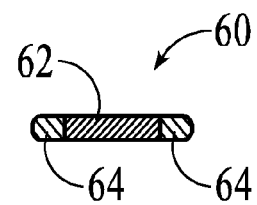
FIG. 5A     FIG. 5B

SYSTEMS AND METHODS FOR TRANSCUTANEOUSLY IMPLANTING MEDICAL DEVICES

RELATED APPLICATION

The present application claims priority to U.S. provisional patent application No. 61/470,454 filed Mar. 31, 2011, entitled "Systems and Methods for Transcutaneously Implanting Medical Devices", the disclosure of which is incorporated herein by reference for all purposes.

BACKGROUND

The introduction and temporary implantation through the skin, e.g., transcutaneously, percutaneously and/or subcutaneously, of biosensors has become very common in the treatment of patients inflicted with or suffering from any one of many different types of conditions. These implantable sensors include those monitoring a given parameter that indicates a certain bodily condition, e.g., a patient's glucose level, or the actual state of a treatment, e.g., monitoring the concentration of a drug dispensed to the patient or a body substance influenced by the drug.

In recent years, a variety of temporarily implantable sensors have been developed for a range of medical applications for detecting and/or quantifying specific agents, e.g., analytes, in a patient's body fluid such as blood or interstitial fluid. Such analyte sensors may be fully or partially implanted below the epidermis in a blood vessel or in the subcutaneous tissue of a patient for direct contact with blood or other extra-cellular fluid, such as interstitial fluid, wherein such sensors can be used to obtain periodic and/or continuous analyte readings over a period of time.

Certain transcutaneous analyte sensors have an electrochemical configuration in which the implantable portion of these sensors includes exposed electrodes and chemistry that react with a target analyte. At an externally located proximal end of the sensor are exposed conductive contacts for electrical connection with a sensor control unit which is typically mountable on the skin of the patient. One common application of such analyte sensor systems is in the monitoring of glucose levels in diabetic patients. Such readings can be especially useful in monitoring and/or adjusting a treatment regimen which may include the regular and/or emergent administration of insulin to the patient.

A sensor insertion device or kit is typically provided with such analyte monitoring systems for inserting the sensor into a patient. The insertion kit includes an introducer which typically has a sharp, rigid structure adapted to support the sensor during its transcutaneous insertion. Some introducers are in the form of needles having a slotted or hollow configuration in which a distal portion of the sensor is slidably carried to the desired implantation site, e.g., subcutaneous site, after which the insertion needle can be slidably withdrawn from the implanted sensor. Often, the insertion kit also includes an insertion gun for automatically or semi-automatically driving the introducer and attached sensor to within the skin. Implantation of a sensor with such an insertion device typically involves using the insertion gun to drive the introducer and pre-loaded sensor into the skin of the patient. The introducer is retracted into the insertion gun, leaving the sensor implanted within the patient.

While such sensor insertion tools can greatly assist a user in effectively and efficiently implanting transcutaneous sensors, they are not without their drawbacks. As they are designed to be substantially automatic, the insertion guns tend to be mechanically complex, involving numerous static and moving parts. With the added complexity of such tools are significant costs in designing and fabricating them, contributing significantly to the overall cost of the sensor systems. In addition to the financial and manufacturing-related drawbacks, there are significant clinical consequences to using such transcutaneous sensor insertion tools.

The subcutaneous or other placement of such sensors, or any medical device, produces both short-term and longer-term biochemical and cellular responses which may lead to the development of a foreign body capsule around the implant. Consequently, this encapsulation may reduce the flux of an analyte to the sensor, i.e., may reduce the sensitivity or accuracy of the sensor function, often requiring numerous calibrations over the course of the sensor's implantation period. The extent of the immune response presented by implantable sensors, as well as the amount of pain and discomfort felt by the patient, are exacerbated by the size of the sensor introducer and/or the implantable portion of the sensor, often referred to as the sensor tail. With sensor introducers that carry the sensor within an interior or substantially interior space, there is naturally a limit on the extent to which the cross-sectional dimension of the introducer can be reduced.

Accordingly, it would be highly desirable to provide a sensor introducer and associated sensor design, and/or a combined assembly, which do not require a separate insertion tool for their transcutaneous insertion, thereby minimizing the number of components involved, and reducing mechanical complexity and manufacturing costs. It would be additionally advantageous if the respective and combined dimensions and configurations of the introducer and sensor were further reduced to minimize the trauma, pain and immune response to sensor insertion/implantation.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,676,819; 6,730,200; 6,736,957; 6,746,582; 6,749,740; 6,764,581; 6,773,671; 6,881,551; 6,893,545; 6,932,892; 6,932,894; 6,942,518; 7,167,818; 7,299,082; 7,381,184; 7,618,369, 7,697,967 and 7,885,698; U.S. Published Application Nos. 2004/0186365; 2005/0182306; 2007/0056858; 2007/0068807; 2007/0227911; 2007/0233013; 2008/0081977; 2008/0161666; 2009/0054748; 2009/0247857; and 2010/0081909; and U.S. patent application Ser. Nos. 11/396,135, 11/537,984, 12/131, 012; 12/242,823; 12/363,712; 12/698,124; 12/714,439; 12/807,278; 12/842,013; and 12/848,075.

SUMMARY

Embodiments of implantable medical devices and of methods, systems and devices for positioning at least a portion of the medical devices beneath the epidermal layer of skin, e.g., transcutaneously, are described. A portion or the entirety of the medical devices may be implanted in a blood vessel, subcutaneous tissue, or other suitable body location. Certain embodiments of the implantable medical devices are in vivo analyte sensors for the continuous and/or automatic detection and measurement of one or more selected analytes.

Certain system embodiments configured for transcutaneously implanting a medical device include an introducer having at least a portion engageable with at least a portion of the medical device, wherein the introducer is at least partially formed from a shape memory material, and an activating component to activate the introducer to transition from a first operative shape memory state to a second operative shape memory state, wherein said transition translates the medical device engaged with the introducer from a position above the skin surface to at least partially through the skin surface. In certain of these embodiments, the first operative shape memory state is a heat-unstable shape and the second operative shape memory state is a heat-stable shape, wherein the activating component may include an electrical current generating component electrically coupled to the introducer.

In certain aspects of these system embodiments, the first operative shape memory state is a physically loaded configuration and the second operative shape memory state is a physically unloaded configuration, wherein the activating component may include a driving mechanism mechanically coupled to the introducer.

In certain embodiments, the subject systems may include a housing configured for placement on a skin surface of a host, wherein the introducer is configured to be at least partially positioned within the housing when in the first operative shape memory state. The housing may include a compartment within which the introducer is configured to be at least partially contained when in the first operative shape memory state.

In certain embodiments, the portion of the introducer engageable with the medical device defines a major axis wherein during the transition from the first operative shape memory state to the second operative shape memory state, the introducer changes shapes along the major axis. Further, in certain embodiments, the subject introducers may have at least one coupling member for securing the medical device to the introducer at least when in the first operative memory state. The shape memory materials suitable for fabricating the subject introducers include, but are not limited to, nickel-titanium, copper-zinc-aluminum-nickel, copper-aluminum-nickel, and alloys of zinc, copper, gold and iron.

In a particular system of the present disclosure adapted for transcutaneously implanting a medical device, the system includes a housing configured for placement on a skin surface of a host, an introducer configured to be at least partially positioned within the housing and having at least a portion engageable with at least a portion of the medical device, wherein the introducer is at least partially formed from a shape memory material, and an electrical current generating component electrically coupled to the introducer for activating the introducer to transition from a heat-unstable shape to a heat-stable shape, wherein said transition translates the medical device engaged with the introducer from a position within the housing to at least partially through the skin surface. The electrical current generating component may include a battery contained within the housing, which battery may also be used to power a control unit for operating the medical device. In other embodiments, the battery may be provided separately, i.e., not contained within the housing.

In other embodiments for transcutaneously implanting a medical device, a system may include a housing configured for placement on a skin surface of a host, an introducer configured to be at least partially positioned within the housing and having at least a portion engageable with at least a portion of the medical device, wherein the introducer is at least partially formed from a shape memory material, and a driving mechanism mechanically coupled to the introducer for moving the introducer relative to the housing in order to transition from a loaded configuration to an unloaded configuration, wherein said transition translates the medical device engaged with the introducer from a position within the housing to at least partially through the skin surface. The system housing may include a compartment configured to physically retain the introducer in the loaded configuration.

The present disclosure is also directed to an in vivo analyte monitoring system including a housing configured for placement on a skin surface of a host, a control unit housed within the housing, an in vivo analyte sensor having a proximal portion and a distal portion, wherein the proximal portion is operatively coupleable to the control unit, a sensor introducer at least partially positioned within the housing, wherein the introducer is at least partially comprised of a shape memory material and wherein a portion of the introducer is engageable with the sensor distal portion, and a transitioning component to transition the introducer from a first operative shape memory state to a second operative shape memory state, wherein said transitioning translates the sensor distal portion from a position within the housing to at least partially through the skin surface.

In certain embodiments, the portion of the introducer engageable with the sensor distal portion may have a crosswise dimension substantially similar to, or alternatively different than, that of the sensor distal portion. For example, the portion of the introducer engageable with the sensor distal portion may have a crosswise dimension smaller than that of the sensor distal portion. In certain aspects, the sensor distal portion and the portion of the introducer engageable with the sensor distal portion may have respective configurations which enable a nesting arrangement between them. This engageable portion of the introducer may have any suitable shape when in the first operative shape memory state including but not limited to a U-shaped configuration.

Other features of the introducer may include a distal tip configured to substantially atraumatically pierce the skin surface, and/or at least one coupling member for securing the medical device, e.g., the sensor distal portion, to the introducer at least when the introducer is in the first operative memory state.

The present disclosure includes embodiments directed to transcutaneously implantable medical devices which are substantially self-implanting without the need for a separate introducer or other instrument to facilitate the device's implantation through the skin. In certain embodiments, these medical devices include a flexible, elongated substrate having a distal tip configured to substantially atraumatically pierce the skin surface, wherein the substrate is formed from a non-conductive material, and at least one spine extending along a length of the substrate, wherein the at least one spine is formed from a shape memory alloy, and wherein the medical device is translatable from a first operative shape memory state to a second operative shape memory state. The shape memory material used to fabricate these medical devices may include, but are not limited to, one or more of nickel-titanium, copper-zinc-aluminum-nickel, copper-aluminum-nickel, and alloys of zinc, copper, gold and iron. Depending, at least in part, on the type of shape memory material employed, the first operative shape memory state of the medical device may be a heat-unstable shape and the second operative shape memory state may be a heat-stable shape. In certain embodiments, the first operative shape memory state is a compressed configuration and the second operative shape memory state is an uncompressed configuration.

The construct of these self-inserting medical devices, in certain embodiments, enable them to function as electrochemical sensors. In certain embodiments, one or more of the spines may also function as an electrode. These electrochemical sensors may include analyte sensors, such as glucose sensors.

The present disclosure is also directed to methods for transcutaneously implanting a medical device. In certain embodiments, at least a portion of the medical device is flexible. Such methods may involve providing an introducer, wherein the introducer is at least partially formed from a shape memory material, engaging at least the flexible portion of the medical device with the introducer, wherein the engaged introducer and medical device are in a nested arrangement, and wherein when the introducer is in a first operative shape memory state, positioning a skin-penetrating end of the introducer adjacent to the skin surface, and transitioning the introducer from the first operative shape memory state to a second operative shape memory state, wherein the introducer penetrates through the skin surface and transcutaneously implants at least a portion of the flexible portion of the medical device beneath the skin surface.

In certain embodiments of the above-described method, transitioning the introducer from the first operative shape memory state to the second operative shape memory state includes applying an electrical current to the introducer. In certain embodiments, the step of engaging the flexible portion of the medical device with the introducer in a nested arrangement includes cooling the introducer to a predefined temperature while the medical device is structurally aligned along a major axis of the introducer.

In certain embodiments of the above-described method, transitioning the introducer from the first operative shape memory state to the second operative shape memory state includes releasing the introducer from a confined space. As such, the step of engaging the flexible portion of the medical device with the introducer in a nested arrangement may include loading the introducer to a reduced profile while the medical device is structurally aligned along a major axis of the introducer and positioning the introducer and nested sensor in the confined space. This confined space may be provided within a housing that is configured for placement on the skin surface.

The subject methods may also include the removal of one or both the introducer and medical device from the skin subsequent to implantation. In certain embodiments, the methods may further include removing the introducer from the skin while leaving the transcutaneously implanted medical device within the patient, or alternatively, maintaining the introducer within the skin along with the transcutaneously implanted medical device for the useful life of the medical device. Such explantation of the introducer and/or introducer and medical device, for example, may be accomplished via manual retraction or by transitioning the introducer from the second operative shape memory state back to the first operative shape memory state.

These and other objects, advantages, and features of the disclosure will become apparent to those persons skilled in the art upon reading the details of the disclosure as more fully described below.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 3A shows the introducer and sensor in operative engagement in a first or pre-insertion state and FIG. 3B shows the introducer and sensor in operative engagement in a second or post-insertion state;

FIG. 4A is an enlarged fragmented view of a distal end portion of one embodiment of a sensor of the present disclosure;

FIG. 4B is a cross-sectional view of the sensor of FIG. 4A taken along line B-B;

FIG. 5A is an enlarged fragmented view of a distal end portion of one embodiment of a sensor of the present disclosure; and FIG. 5B is a cross-sectional view of the sensor of FIG. 5A taken along line B-B.

DETAILED DESCRIPTION

Figure 1A:
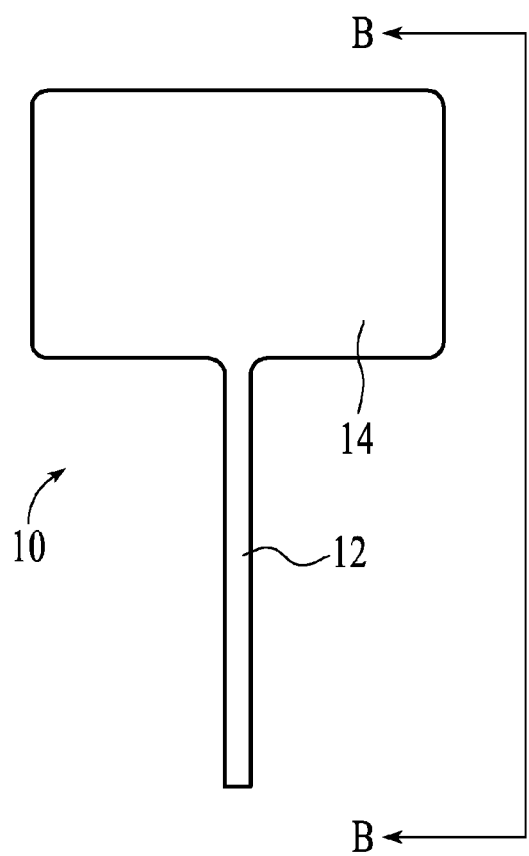
FIGS. 1A and 1B are front and side views, respectively, of a transcutaneously implantable sensor of the present disclosure, where the views are taken along lines A-A and B-B, respectively, of the other Figure.

Before the subject devices, systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. As used herein, the terms transcutaneous, subcutaneous and percutaneous and forms thereof may be used interchangeably.

All publications mentioned herein are incorporated herein by reference to disclose and describe the methods and/or materials in connection with which the publications are cited. It is understood that the present disclosure supersedes any disclosure of an incorporated publication to the extent there is a contradiction. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Generally, the present disclosure is directed to transcutaneously implantable or partially implantable medical devices and to devices, systems and methods for transcutaneously implanting such implantable devices. In certain embodiments, the present disclosure is directed to implantable medical devices which are configured to be substantially self-implanting without the need for a separate skin-penetrating structure. While embodiments of the subject disclosure are primarily described below with respect to analyte sensors and analyte monitoring devices, systems and methods, such as for glucose monitoring, such description is in no way intended to limit the scope of the disclosure. It is understood that the subject disclosure is applicable to any medical device in which at least a portion of the device is intended to be implanted within the body of a patient.

Figure 1B:
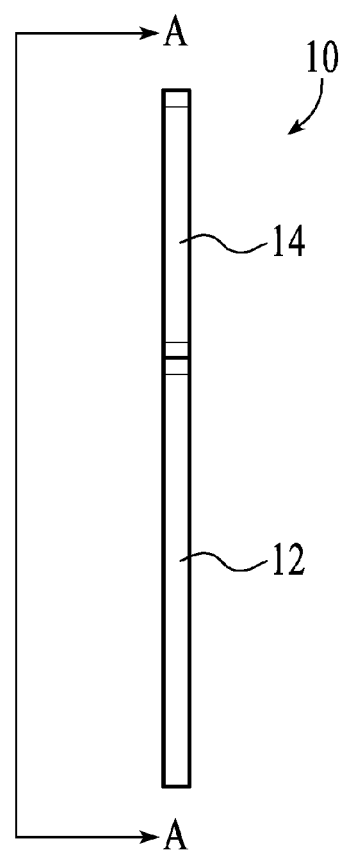

Referring now to the drawings and to FIGS. 1A and 1B in particular, there is shown an embodiment of a partially implantable sensor 10 of the present disclosure. Embodiments of sensor 10 are for the in vivo monitoring or measurement of a physiological condition or state or of a value of a naturally-occurring or unnaturally-occurring substance or agent within the body. As such, sensor 10 may be an analyte sensor (electrochemical, optical, etc.) wherein at least a portion of the sensor is positionable beneath the skin of the user or host for the in vivo determination of a concentration of an analyte in a body fluid, e.g., interstitial fluid, blood, urine, etc. Alternatively or additionally, sensor 10 may be positionable in a body vessel such as a vein, artery, or other portion of the body. Sensor 10 may also have an ex vivo portion which is positionable outside the body, i.e., above the skin surface, and configured to be coupled to a component of a medical device system such as to a control unit 34 mounted on the skin of a patient (see FIGS. 3A and 3B). The intended site and depth of implantation may affect the particular shape, components and configuration of sensor 10 and its in vivo and ex vivo portions, respectively. Examples of such sensors and associated analyte monitoring systems can be found in U.S. Pat. Nos. 6,134,461; 6,175,752; 6,284,478; 6,560,471; 6,579,690; 6,746,582; 6,932,892; 7,299,082; 7,381,184; 7,618,369, 7,697,967 and 7,885,698; and U.S. Patent Application Publication Nos. 2008/0161666, 2009/0247857 and 2010/0081909, the disclosures of each of which are incorporated herein by reference.

Although the subject sensors in at least some embodiments have uniform dimensions along the entire length of the sensor, in the illustrated embodiment, sensor 10 has a distal portion 12 and a proximal portion 14 with different widths. Distal portion 12, also referred to as the tail portion of the sensor, has a relatively narrow width to facilitate subcutaneous implantation of at least a portion of its length, while proximal portion 14 has a relatively wider width to facilitate coupling with an external control unit 34 (see FIGS. 3A and 3B). In certain embodiments, distal portion 12 is substantially narrower than proximal portion 14, having a strip-like or wire-like configuration, while proximal portion 14 has a substantially flat, planar configuration. The cross-wise dimension, i.e., the thickness of flat or strip configurations and the diameter of wire-like configurations, of at least distal portion 12 is relatively thin, having a cross-wise dimension in the range from about 0.02 mm (20 μm) to about 1.2 mm (1,200 μm), and more typically from about 0.2 mm (200 μm) to about 0.6 mm (600 μm).

Where sensor 10 is an electrochemical sensor, the sensor includes at least one working electrode formed on a substrate. The sensor may also include at least one counter electrode and/or at least one reference electrode and/or at least one counter/reference electrode. The sensor substrate may be formed using a variety of non-conducting materials, including, for example, polymeric or plastic materials and ceramic materials; however, at least the implantable portion of sensor 10, i.e., at least a portion of distal portion 12, is made of a flexible, bendable and/or deformable material. Suitable materials for a flexible substrate include, for example, thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

Analytes measurable by the subject sensors may include but are not limited to glucose, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. Other of the subject sensors may be configured to detect and measure drugs, such as, for example, antibiotics (e.g., gentamicin, vancomycin, and the like), digitoxin, digoxin, drugs of abuse, theophylline, and warfarin. Two or more analytes and/or drugs may be monitored at the same or different times, with the same or different analyte sensor(s).

Sensors described herein may be configured for monitoring the level of an analyte over a time period which may range from minutes, hours, days, weeks, one month or longer. Of interest are analyte sensors, such as glucose sensors, that have an in vivo operational life of about one hour or more, e.g., about a few hours or more, e.g., about a few days of more, e.g., about three days or more, e.g., about five days or more, e.g., about seven days or more, e.g., about several weeks or months.

As mentioned previously, eliminating the need for a separate sensor insertion tool, e.g., an insertion gun, for transcutaneously implanting the subject sensors would provide the benefits of fewer components, reduced costs, and increased ease of use for a user of such sensors. The present disclosure provides an introducer or inserter (both terms are used interchangeably herein) for transcutaneously implanting a medical device, such as sensor 10, without the need for a separate tool or instrument for driving and/or retracting the introducer through the skin. Instead, the introducer or inserter is driven or translated solely by its shape-shifting material characteristics. More particularly, the subject introducers or inserters are made, at least in part, of a shape memory alloy (SMA) having memory characteristics which function to define one operative configuration which is transitionable or convertible to another operative configuration.

In certain embodiments, the state transition is a reversion from a heat-unstable configuration to an original, heat-stable configuration upon the application of heat to the SMA structure. In the manufacturing process, the original, heat-stable or "austenitic" state of the SMA structure is deformed to a new, heat-unstable or "martensitic" state when cooled below the temperature at which the SMA is transformed from the austenitic state to the martensitic state. The temperature at which this martensitic transformation begins is usually referred to as $M_s$ and the temperature at which it finishes is referred to as $M_f$. When an article thus deformed is heated to the temperature at which the alloy starts to revert back to austenite, referred to as $A_s$ ($A_f$ being the temperature at which the reversion is complete), the deformed object will begin to return to its original, heat-stable configuration. The martensitic and austenitic temperatures of a particular SMA structure are predefined based on the type of SMA material from which the structure is formed.

In other embodiments, the transition of the SMA structure from one operative configuration to another is the reversion of the structure from a physically stressed or confined state to an unstressed, unconfined original state upon the removal of an externally applied force. During the manufacturing process, the SMA structure is formed to a selected unloaded or unstressed shape. When the structure is loaded or stressed, typically by positioning it in a confined space, typically to a lower-profile state, a bias toward the original, unstressed state is created. When the structure is released or the confinement removed, the biased SMA structure returns to its original, unloaded, unstressed condition. This type of memory characteristic is sometimes referred to as superelasticity or pseudoelasticity.

Suitable shape memory alloys for use in the introducers of the present disclosure include but are not limited to nickel-titanium (NiTi), copper-zinc-aluminum-nickel, copper-aluminum-nickel, and other alloys of zinc, copper, gold, and iron.

The subject introducers are structurally configured to accommodate the shape and size of the medical device, such as a sensor, to be transcutaneously positioned. As many medical devices configured for transcutaneous implantation, such as the in vivo analyte sensors discussed herein, are designed to minimize pain and trauma to the patient, their implantable portions are very narrow and elongated. Accordingly, in many embodiments, the subject introducers have a shape and cross-sectional dimension to substantially match those of the medical device, e.g., very narrow and elongated needle-type structure, so as to minimize pain and trauma. However, in certain embodiments, the introducer may have a shape and/or size which are dissimilar to those of the medical device to be implanted. Because minimizing pain and trauma is an important objective in treating patients, in some embodiments, the smaller the introducer, the better. In some cases, the introducer may have a cross-wise dimension that is smaller than that of the medical device as long as the introducer is able to retain the medical device in a compressed condition prior to transcutaneous insertion and to effectively advance it through the skin when activated.

Figure 2A:
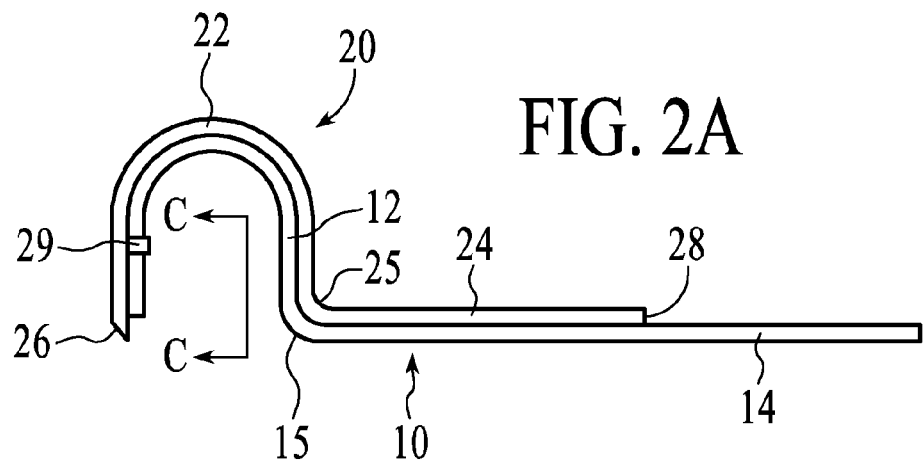
FIG. 2A is a side view of an introducer of the present disclosure with the sensor of FIGS. 1A and 1B operatively engaged with the introducer, collectively in a first or pre-insertion state.
Figure 2B:
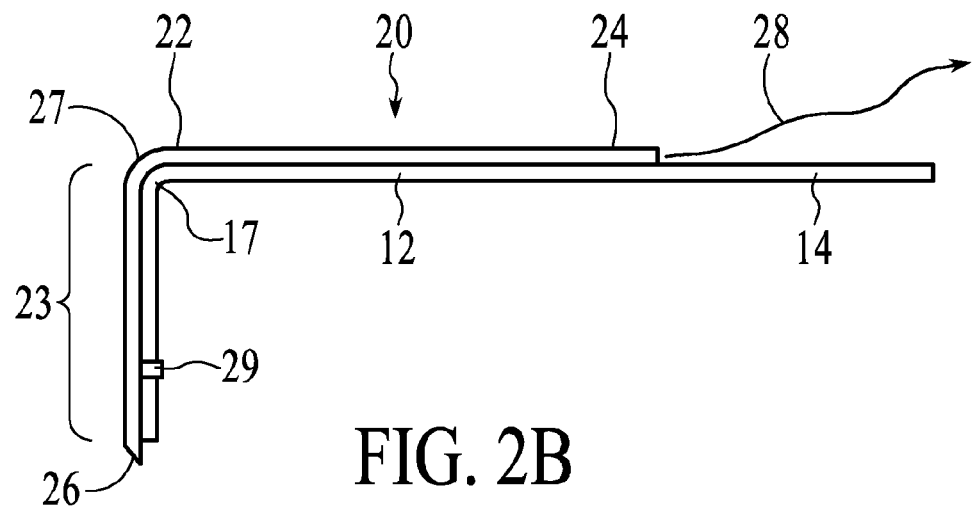
FIG. 2B is a side view of the introducer and sensor of FIG. 2A, collectively in a second or post-insertion state.

For certain of the introducer embodiments of the present disclosure, the subject sensors, such as sensor 10 of FIGS. 1A and 1B, are operatively coupled with the subject introducers prior to implantation of the sensor, wherein the respective major axes of the insertion portion of introducer and the sensor distal or tail portion, i.e., their longitudinal axes, are substantially parallel and in substantial physical contact with each other. The flexibility of the sensor substrate allows it to be engaged with and deformable or bendable in tandem with the introducer as the latter transitions between its heat-unstable and heat-stable states. One such operative engagement between a shape memory introducer 20 of the present disclosure and a medical device, such as sensor 10, is illustrated in FIGS. 2A-2D. In particular, FIG. 2A shows the introducer-sensor assembly in a pre-implantation or pre-insertion state in which at least a distal portion of sensor 10 has been deformed from its naturally flat straight condition, as illustrated in FIGS. 1A and 1B, to a shape in which it nests with inserter 20 when the inserter is in its heat-unstable, martensitic state (in the case of heat-transitionable memory embodiments of the introducer) or in its stressed, loaded or confined state (in the case of the elastic memory embodiments of the introducer). FIG. 2B, on the other hand, shows the inserter-sensor assembly in a post-implantation or post-insertion state in which inserter 20 has been transitioned to its heat-stable, austenitic state (in the case of heat-transitionable memory embodiments of the introducer) or to its unstressed, unloaded or unconfined state (in the case of elastic memory embodiments of the introducer). For purposes of this description, the pre-implantation/pre-insertion state of FIG. 2A may be referred to as a first operative shape memory configuration or shape, and the post-implantation/post-insertion state of FIG. 2B may be referred to as a second operative shape memory configuration or shape.

With reference to FIG. 2A, the first operative shape of inserter 20 includes a U-shaped distal portion 22 transitioning at a bend 25 to a straight proximal portion 24 where the transition bend has an angle of about 90°. The corresponding first operative shape of sensor 10 substantially conforms to that of inserter 20, i.e., sensor distal portion 12 has taken on the U-shape of introducer distal portion 22 and sensor proximal portion 14 has aligned with introducer proximal portion 24 with a transition bend 15 therebetween. Introducer 20 may be configured to have any suitable heat-unstable or elastically-deformable shape or configuration, provided the resulting profile of the introducer-sensor assembly allows it to be positionable within the structure or housing used for delivering or carrying the assembly prior to transcutaneous implantation, as discussed in greater detail below. Accordingly, the pre-implantation introducer-sensor assembly may have any suitable first operative configuration including, but not limited to, V-shaped, C-shaped, coiled, looped, sinusoidal, etc.

With reference to FIG. 2B, the second operative shape of introducer 20 includes a length 23 of distal portion 22 which is shaped for transcutaneous implantation, which length portion 23 is typically substantially straight and substantially corresponds to the length of sensor distal portion 12 which is intended for transcutaneous implantation. As the entire distal portion 12 of sensor 10 is not intended to be implanted, introducer 20, in its second operative state, includes a transition bend 27 within or about distal portion 22 wherein the remaining proximal end portion of introducer 20 has a substantially straight configuration, providing a cooperative L-shaped configuration when in the second operative state. As with the first operative shape of sensor 10, the corresponding second operative shape of sensor 10 is substantially conforming to that of introducer 20, i.e., having a transition bend 17 between distally and proximally extending straight portions. Transition bends 17 and 27 within the sensor and introducer, respectively, may have any suitable angle, wherein the transition angle may be selected to provide a skin penetration path that is substantially transverse to the skin surface, i.e., at about a 90° angle. Alternatively, the transition angle may be in the range from less than 90° degrees to about 135°, but may be more or less, to provide a skin penetration path that is angled with respect to the skin surface.

It is noted that the respective first and second operative configurations of introducer 20 may have any suitable shape for the given application, insertion site, etc., with the respective transition bends 25 and 27 of introducer 20 in the first and second operative configurations provided at any suitable location along the length of the introducer, including within the distal portion 22, as illustrated, or substantially between the distal and proximal portions. Further, bends 25 and 27 may have any suitable angle including angles greater or less than the illustrated 90°. Further, the respective locations of bends 25 and 27 along the length of introducer 20 may differ from each other, as illustrated, or introducer 20 may be configured such that the bends in the first and second operative configurations coincide at the same location along the introducer's length. For example, in the illustrated embodiment, bend 27 in FIG. 2B (when introducer 20 is in the second operative state) is located substantially closer to the distal tip 26 of the introducer than bend 25 in FIG. 2A (when introducer 20 is in the first operative state). In any embodiment, when in the second operative configuration, the length or portion 23 of introducer 20, as well as the corresponding length/portion of sensor 10 extending distally of transition bend 27, are typically those length portions which are positioned beneath the skin surface upon transcutaneous implantation.

Figure 2C:
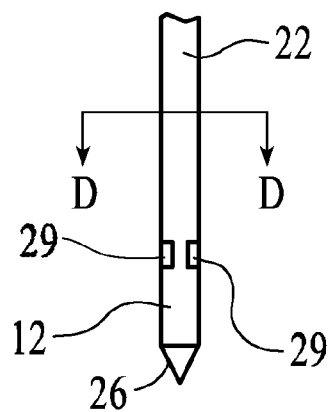
FIG. 2C is an enlarged view of a distal end portion taken along line C-C of FIG. 2A.
Figure 2D:
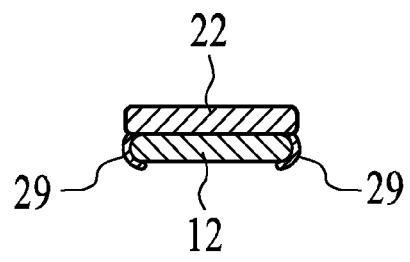
FIG. 2D is a cross-sectional view taken along line D-D of FIG. 2C.

As best illustrated in FIGS. 2C and 2D, introducer 20 may include one or more coupling members 29 for securing sensor 10 to introducer 20 or for guiding sensor 10 along the transcutaneous insertion path enabled by introducer 20 upon implantation. In the illustrated embodiment, the coupling member 29 includes tabs or protrusions positioned on opposing sides of introducer 20 which engage sensor 10 about its width. Coupling member 29 may be positioned at any suitable location along the length of introducer 20, such as about distal portion 22, as illustrated. The securement provided by coupling member 29 may be releasable or permanent. In certain embodiments, introducer 20 is configured and intended to be withdrawn from the skin after transcutaneous insertion of sensor 10. As such, coupling member 29 is configured to enable introducer 20 to be slidably removable from implanted sensor 10. To this end, coupling member 29 may extend laterally from introducer 20 only to the extent necessary to maintain sensor 10 in longitudinal alignment with introducer 20 and function as guides during the pre- and post-implantation states, while allowing introducer 20 to be slidably removed from the skin in a retrograde direction after transcutaneous implantation of sensor 10. In embodiments where introducer 20 is to remain coupled and implanted with sensor 10 after transcutaneous implantation, coupling member 29 may be configured to completely engage sensor 20, and may even fully crosswise encircle the sensor.

It is noted that while a coupling member 29 is provided in the illustrated embodiment, no such member may be needed in certain embodiments where the spring bias placed on flexed sensor 10 via the physical confinement by introducer 20 in the first (and sometimes the second) operative state is sufficient to maintain the sensor's engagement and alignment with the introducer prior to and during its transcutaneous implantation. To provide such sufficient spring-biased engagement between the sensor and the introducer, the sensor may need to be nested within or constrained in a somewhat confined space or plane defined by the introducer, at least when in the first operative state, as illustrated in FIG. 2A. More specifically, sensor 10 is nested within the concave side of introducer 20, where such "nesting" may place a sufficient spring bias along the longitudinal axis of sensor 10 to maintain its static position against the introducer prior to and during transcutaneous insertion.

In certain embodiments, the size of an SMA introducer is comparable to the size of the device to be transcutaneously implanted, i.e., the larger the sensor, the larger the introducer. The introducer should not be any larger than necessary as the larger the introducer, the more energy (i.e., electrical current or physical force) required to activate the shape transition of the introducer. However, the introducer should be large enough to enable the sensor to penetrate the skin without bearing much frictional resistance. Accordingly, introducers for use with the sensors having the dimensions described previously herein will have comparable cross-sectional dimensions (i.e., thicknesses or diameters). For example an SMA introducer with the same or substantially similar cross-sectional area as the previously described sensors can exhibit a one-time force of over 6 kg. That much force applied to an introducer having a pointed or sharpened tip 26, as shown in FIGS. 2A and 2B, would be more than sufficient to penetrate skin.

In addition to comparable sizes, the crosswise shape of introducer 20 may be identical or similar to that of sensor 10, such as illustrated in FIG. 2D, where both the introducer and sensor have a strip or flat rectangular configuration. Alternatively, the two components may each have a crescent or C-shape to facilitate their "nesting" engagement. In other embodiments, the sensor and introducer may have different cross-sectional shapes, where the shapes have respective mating configurations to also facilitate "nesting" of the sensor with the introducer. For example, the introducer may have a concave surface which engages with a corresponding convex surface of the sensor. Their respective outer or non-contacting surfaces may both be convex to facilitate penetration into the skin. Still yet, in certain embodiments, the crosswise configuration and size of introducer 20 may be substantially different from that of sensor 10. For example, the introducer may have a wire configuration with a relatively small cross-sectional surface area as compared to that of the sensor, provided the mass of the wire introducer is sufficient to conform the sensor into the predefined operative states.

It is noted that due to the metallic and, thus, conductive nature of introducer 20, care should be taken to ensure that the electrodes of sensor 10 (in electrochemical embodiments) are insulated from introducer 20. This may be accomplished by providing an insulative coating around either or both sensor 10 and introducer 20, while ensuring that such a coating does not in any way obstruct exposure of the sensing portion of the sensor electrodes to the subcutaneous environment.

In certain embodiments, introducer 20 is configured at its proximal end 24 to couple, mate or engage with an activation mechanism or component 28 (illustrated schematically) for activating a transition from the first operative state of FIG. 2A to the second operative state of FIG. 2B. The construct and the type of energy/force imparted by activation component 28 is dependent upon the type of memory function employed by introducer 20. For introducers 20 having a heat-transitionable memory, activation component 28 may be an electrical coupling to a source of electrical power for conducting an electrical current to introducer 20 which heats the introducer SMA material to a temperature sufficient to transition the introducer from its heat-unstable martensitic state (i.e., the first operative state of FIG. 2A) to its heat-stable austensitic state (i.e., the second operative state of FIG. 2B). For introducers 20 having an elastic memory, activation component 28 may include a mechanical coupling between introducer 20 and a driving mechanism for imparting a physical force on introducer 20 sufficient to translate it out from a physically confining space, such as within a housing of an on-skin unit as illustrated in FIGS. 3A and 3B, in order to transition the introducer from its loaded, stressed configuration (i.e., the first operative state of FIG. 3A) to its unloaded, unstressed configuration (i.e., the second operative state of FIG. 3B).

Figure 3A:
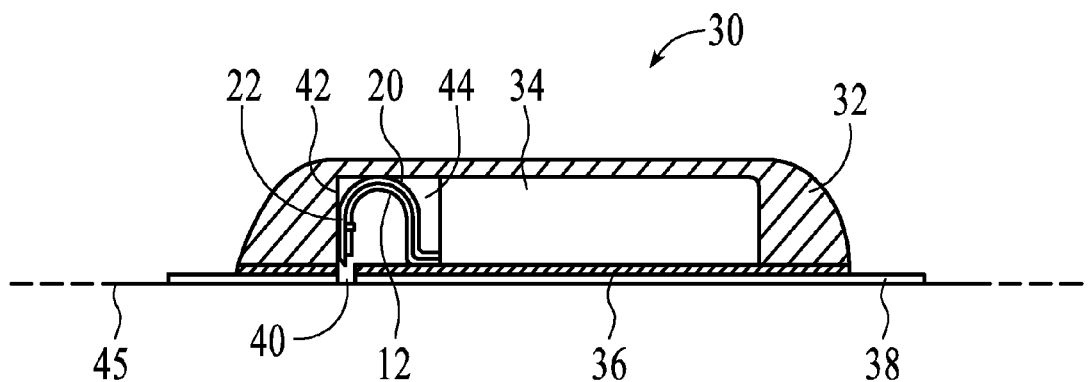
FIGS. 3A and 3B are side cross-sectional views of a sensor system of the present disclosure operatively mounted on the skin of a patient, where
Figure 3B:
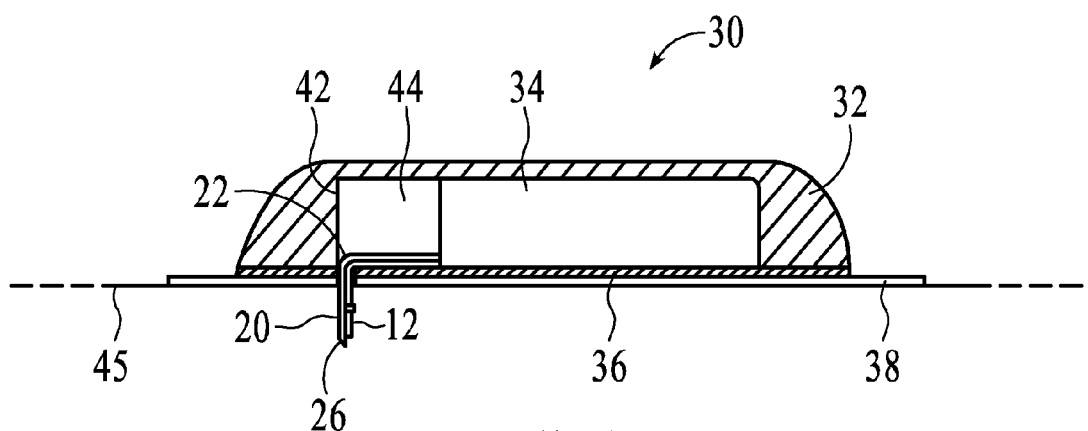

Referring now to FIGS. 3A and 3B, there is shown an analyte monitoring system 30 in which operatively assembled sensor 10 (see FIG. 2A) and introducer 20 are shown operatively coupled to a sensor control unit 34 contained within an on-skin/on-body housing 32. Control unit 34 may provide most or all of the electronic components of an analyte monitoring system including, but not limited to, data processing and communication electronics, the latter of which may include a transmitter for relaying or providing data obtained using the sensor to a remotely located device. The control unit 34 may also include a variety of optional components, such as, for example, a receiver, a power supply (e.g., a battery), an alarm system, a display, a user input mechanism, a data storage unit, a watchdog circuit, a clock, a calibration circuit, etc. A remote unit (not shown), if employed with the on-skin control unit 34, may include one or more of the same components and/or additional components such as an analyte measurement circuit for use with a test strip sensor, a pager, a telephone interface, a computer interface, etc. Examples of such are provided in the patents and patent applications incorporated by reference above.

Housing 32 preferably has a low-profile configuration to provide comfort to the patient or user and enable easy concealment. Housing 32 may include a base or mounting structure 36 which is configured for releasable engagement with the skin surface 45, such as by an adhesive layer, patch or strip 38, or by strapping it to the body. Housing 32 is further configured to provide or facilitate physical and/or electrical coupling between the proximal portion of sensor 10 (not shown in FIGS. 3A and 3B) and control unit 34, as well as to electrically and/or mechanically couple proximal portion of introducer 20 to an activation component 28 (see FIGS. 2A and 2B; not shown in FIGS. 3A and 3B). The respective distal portions 12, 22 of sensor 10 and introducer 20 extend from control unit 34 to within a chamber or compartment 44 within housing 32. An aperture 40 is provided within mounting structure 36 and adhesive layer 38 to allow for the extension therethrough of engaged and nested sensor and introducer distal portions 12, 22 when introducer 20 is caused to transition from the first operative or contained state of FIG. 3A to the second operative or extended or implanted state of FIG. 3B by the introducer's SMA memory function.

The introducer transition activation component 28, as discussed above, may be an electrical and/or mechanical component depending on the type of memory function employed by the particular introducer 20, and may be physically housed within or coupled to or associated with housing 32 and/or control unit 34.

For introducer embodiments having heat-transitionable memory capabilities, the proximal end 24 of introducer 20 is coupled to an electrical activation component. In certain of these embodiments, the activation component is an electrical power source, e.g., a battery or power circuit, and/or the associated electrical coupling housed within housing 32 and/or control unit 34. System 30 may be configured such that when control unit 34 is turned on, subsequent to operative mounting of the on-skin unit, an electrical current is provided from the battery or power circuit to introducer 20 by electrical coupling between the two. Such electrical coupling may be a wire or an electrical contact extending between the proximal portion 24 of introducer 20 and the power source, or proximal portion 24 may be directly electrically coupled to the power source. The amount of current supplied to introducer 20 is sufficient to result in a temperature rise sufficient to trigger the martensitic-to-austensitic shape change, which physical change in introducer 20 causes it, along with nested/coupled sensor 10, to be forced downward through housing aperture 40 and through the adjacent skin surface 45 (see FIG. 3B). The activation/transition temperature should have a minimum value sufficiently greater than the range of possible ambient temperatures to avoid unintentional activation of the introducer's shape change, but otherwise should have a maximum value as low as possible to minimize the amount of energy required to activate it. In certain embodiments, the activation temperature of SMA introducer 20 is just below body temperature (37° C.) so that activation and transcutaneous insertion occurs automatically very shortly after the on-body control unit housing 32 is attached to the skin. The maximum heat generated in the introducer should not exceed a temperature which may feel uncomfortable to the user, cause burning of or damage to the user's skin or tissue, or cause damage to the medical device, such as sensor 10, to which the introducer is engaged.

The electrical current necessary to activate a heat-transitional SMA introducer of the present disclosure will vary depending on the size, i.e., cross-sectional dimension, of the introducer. More specifically, the minimum required current ($I_{M-A}$) to produce or activate the requisite temperature to initiate the martensitic-to-austenitic transition of SMA structures is generally represented by the linear equation $$I_{M-A} \text{ (amps)}=0.25 \times 10^{-4} \text{ (amps/}\mu m^2) \times A \text{ (}\mu m^2\text{)},$$

where A is the average cross-sectional area of the SMA structure. Accordingly, for introducers having sizes suitable for implantation of the sensors described above, i.e., having cross-sectional areas in the range from about 400 $\mu m^2$ to about 1,440×10³ $\mu m^2$, and more typically from about 40×10³ $\mu m^2$ to about 360×10³ $\mu m^2$, the activation current will range from about 0.01 amps to about 36 amps, and more typically from about 1 amp to about 9 amps, but may be higher or lower depending on the size of the introducer. In one particular embodiment in which a the sensor distal section has a rectangular cross-section with a thickness of about 200 $\mu m$, a width of about 600 $\mu m$, and a resulting cross-sectional area of about 120×10³ $\mu m^2$, and the corresponding SMA introducer has substantially similar dimensions, the activation current range is about 3 amps.

Typically, the activation current need only be supplied to the introducer for less than a second (i.e., milliseconds) to create the shape transition in the introducer and to drive the sensor into the skin. When the temperature of the SMA introducer reaches a temperature above ambient temperature, it begins to cool spontaneously through free convection. For efficiency and power conservation reasons, then, it is advantageous to heat the introducer to its transition temperature as quickly as possible. The larger the control unit battery, the greater the possible output current and the faster the introducer is heated. However, to avoid adding unwanted weight and mass to the on-body control unit with a larger battery, a super capacitor may be placed in a parallel circuit with a smaller battery to insulate the battery from the high power draw of the SMA introducer. Alternatively, a separate hand-held battery pack may be provided which is used only initially upon operative placement of the on-body control unit to activate the SMA introducer. After transcutaneous insertion of the sensor, the battery pack may be unplugged from the control unit and the on-board, internally housed smaller battery employed to operate the device.

In certain embodiments, introducer 20 may include an insulative layer to protect the patent or user and/or the medical device, such as sensor 10, from heat or electrical damage due to the current and subsequent temperature increase provided to introducer 20 to transition from the first operative state to the second operative state.

Pursuant to certain introducer embodiments providing an elastic memory function, proximal end 24 of introducer 20 is coupled to a mechanical activation component (not illustrated). When activated, the mechanism axially drives or moves introducer 20 such that it is caused to forcibly abut the side and/or overhead interior walls 42 of compartment 44 (see FIG. 3A) which, in turn, forces at least distal portion 22 of introducer 20 and nested sensor 10 through housing aperture 40. Alternatively, compartment 44 may have a construct different than the one illustrated, and a mechanical driving force other than an axial force may be placed upon introducer 20 in order to initiate the displacement of it through aperture 40. In either case, the mechanical activation component may be activated automatically upon turning on control unit 34 or may be triggered manually by a switch or button (not shown) provided on the outer surface of housing 32. Upon release from the confinement of compartment 44, the loaded introducer structure 20 reverts to its unstressed, unconfined original state which drives it into the skin surface 45 (see FIG. 3B).

With any of the above described embodiments, system 30 may be configured such that introducer 20 is automatically retracted or removed from the skin 45 immediately upon transcutaneous placement of sensor 10 while leaving sensor 10 transcutaneously implanted. In the heat-transitionable memory embodiments of introducer 20, cessation of the current supply to introducer 20 initiates a cooling of introducer 20 to a temperature which commences the shape conversion from the second operative state, i.e., the heat-stable austenitic state, to the first operative state, i.e., the heat-unstable martensitic state, thereby removing itself from the skin and back into compartment 44. In certain embodiments, the cooling process may be expedited to transition introducer 20 from the second operative state back to the first operative state. Because the transcutaneous application and the subcutaneous environment in which introducer 20 is employed, the temperature ranges in which the introducer changes shape, in certain embodiments, will be relatively narrow, e.g., from about 45° C. (for introducer removal) to about 65° C. (for introducer insertion), but may have a narrow or wider temperature range. In the elastic memory introducer embodiments, removal of the introducer may be effected mechanically (not shown), e.g., by utilizing an extension spring or the like, which pulls or lifts introducer 20 in a retrograde direction, i.e., in a direction opposite to its entry into the skin, thereby retrieving the distal portion 22 extending from aperture 40 back into compartment 44. Such a mechanical removal approach may also be used for heat-transitionable introducer embodiments in lieu of having to electrically reactivate the introducer and, in certain embodiments, reconnect the ancillary battery pack.

Alternatively, with introducers of either type of memory function, system 30 may be configured such that introducer 20 remains implanted with sensor 10 for the useful life of the sensor, and is removed along with the sensor upon sensor expiration. While a heat-transitionable SMA introducer may be configured to remove itself as well as the sensor from the implant site, i.e., to transition it from the second operative or austenitic shape back to the first operative or martensitic shape, it may be more efficient and less complicated and costly to simply employ a mechanical retraction component to retract the coupled introducer and sensor back into compartment 44 of housing 32. The same mechanical activation component used for transitioning an elastic memory introducer to a transcutaneously implanted condition may be used to reversibly transition the introducer whereby it is retracted from the skin back into compartment 44. Still yet, systems employing either type of SMA introducer may be configured such that the coupled introducer and sensor are merely pulled out of the skin insertion site along with manual removal of housing 32 from the skin.

Referring now to FIGS. 4A and 4B and FIGS. 5A and 5B, two other sensors 50 and 60 of the present disclosure are provided which are configured to include a feature or structure which enables the respective sensor to be completely self-implanting, i.e., advanced from an on-skin housing/unit to a desired transcutaneous position without the use of a separate introducer, such as introducer 20. Referring to the Figures, in certain embodiments, a member 54 or members 64 made of a shape-shifting material, such as nitinol (NiTi) or another SMA, are provided along at least a portion of the length of the respective sensor substrates 52 and 62, the latter being made of one or more flexible materials discussed above with respect to sensor 10. As such, the respective members 54, 64 function as "spines" to facilitate translation or movement of sensors 50, 60 and, along with pointed substrate tips 56, 66, facilitate penetration of sensors 50, 60 through the skin surface. With sensor 50, for example, a single SMA spine 54 extends substantially along the central axis on one side of sensor 50. With sensor 60, two parallel, spaced apart spines 64 extend along opposing sides of sensor 60. However, any suitable number and location of the spines may be employed on a particular sensor.

The SMA spine(s) may have the heat-transitionable and/or elastic memory characteristics discussed above with respect to introducer 20 and, as such, enable sensors 50, 60 to itself take on the first and second operative states discussed above with respect to introducer 20 but without the assistance of an introducer. In heat-transitionable memory sensor embodiments, spines 54, 64 are electrically coupled to a source of electrical power in a manner similar to that described above with respect to introducer 20, with the coupling to the power source being, in certain embodiments, for example, directly through the control unit of the system. However, the temperature for converting sensors 50, 60 back to the first operative state in order to effect retraction from skin, is likely to be below body temperature, otherwise, the sensors will not remain implanted, but immediately or imminently retract themselves upon cessation of current to their respective spines 54, 64. In elastic memory sensor embodiments, spines 54, 64 are coupled to a mechanical driving mechanism at proximal ends in a manner similar to that described above with respect to introducer 20, with transcutaneous implantation and retraction of sensor 50 being similar as well.

Because of the metallic nature of SMA materials, spines 54, 64 may double as functional electrodes of their respective sensors 50, 60 in the electrochemical sensing of an analyte. In heat-transitional embodiments of such aspects of the present disclosure, spines 54, 64 would function to first translate or drive sensors 50, 60 transcutaneously into the skin and, upon cessation of the driving electrical current through it, would function as analyte sensing electrodes, e.g., as either a working, reference and/or counter electrode.

As shown in the cross-sectional view of FIG. 4B, spine 54 may be embedded within a surface of substrate 52 so as to provide sensor 50 with a flush exterior. Alternatively, spine 54 may lie on a surface of substrate 52 or, as shown in FIG. 5B, spine 64 may form one or more portions or sides of the overall sensor construct. The substrate surface on which or within which the spines is/are provided may be a major surface, as in FIG. 4B, i.e., extending the width side of the sensor substrate, or may be a minor surface, as in FIG. 5B, i.e., extending across the thickness of the sensor substrate. The respective spines 54, 64 extend from a proximal end of sensor 50, 60 (not shown) to a distal portion to the extent necessary to provide the necessary leverage (by mass and/or force) to operatively translate sensors 50, 60.

Sensors 50 and 60 may be fabricated by one or more extrusion methods. For example, the sensor substrate material 52, 62 may be made of a polymer material which may be formed in the desired shape by an extrusion process, in which case, the sensing components, including the conductive materials, as well as the SMA spines 54, 56 are formed or provided on the substrate material after extrusion. In still other embodiments, the subject sensors may be fabricated by an extrusion process in which the SMA spines and the non-conductive materials, e.g., dielectric material forming the substrate, are co-extruded. The substrate-spine structures may then be treated to provide the desired memory characteristics, either temperature-based or elastic types, to the SMA material of the spines. Subsequently, the remaining conductive materials, e.g., metal material forming the electrode and traces, are then formed thereon. Still yet, all of the conductive and non-conductive materials and components may be formed in a single extrusion process. Examples of sensors fabricated by extrusion methods are disclosed in U.S. Patent Application Publication Nos. 2010/0331728; 2010/0331771; 2010/0326842; 2010/0326843; and 2010/0331643; all of which are assigned to the assignee of the present disclosure and are incorporated herein by reference in their entireties.

Certain embodiments of the present disclosure may include system for transcutaneously implanting a medical device, the system comprising an introducer having at least a portion engageable with at least a portion of a medical device, wherein the introducer is at least partially formed from a shape memory material, and an activating component to activate the introducer to transition from a first operative shape memory state to a second operative shape memory state, wherein said transition translates the medical device engaged with the introducer from a position above the skin surface to at least partially through the skin surface.

In certain aspects, the first operative shape memory state may comprise a heat-unstable shape and the second operative shape memory state comprises a heat-stable shape.

In further aspects, the activating component may comprise an electrical current generating component electrically coupled to the introducer.

In certain aspects, the first operative shape memory state may comprise a loaded configuration and the second operative shape memory state comprises an unloaded configuration.

In certain aspects, the activating component may comprise a driving mechanism mechanically coupled to the introducer.

Certain aspects may further comprise a housing configured for placement on a skin surface of a host, wherein the introducer is configured to be at least partially positioned within the housing when in the first operative shape memory state.

In certain aspects, the housing may comprise a compartment within which the introducer is configured to be at least partially contained when in the first operative shape memory state.

In certain aspects, the shape memory material may comprise one or more of nickel-titanium, copper-zinc-aluminum-nickel, copper-aluminum-nickel, and alloys of zinc, copper, gold and iron.

In certain aspects, the portion of the introducer engageable with the medical device may define a major axis wherein, during the transition from the first operative shape memory state to the second operative shape memory state, the introducer changes shapes along the major axis.

In certain aspects, the medical device may comprise an in vivo sensor.

In certain aspects, the introducer may comprise at least one coupling member for securing the medical device to the introducer at least when in the first operative memory state.

Certain embodiments of the present disclosure may include a system for transcutaneously implanting a medical device, the system comprising a housing configured for placement on a skin surface of a host, an introducer configured to be at least partially positioned within the housing and having at least a portion engageable with at least a portion of a medical device, wherein the introducer is at least partially formed from a shape memory material, and an electrical current generating component electrically coupled to the introducer for activating the introducer to transition from a heat-unstable shape to a heat-stable shape, wherein said transition translates the medical device engaged with the introducer from a position within the housing to at least partially through the skin surface.

In certain aspects, the electrical current generating component may comprise a battery contained within the housing.

In certain aspects, the battery may be further configured to power a control unit for operating the medical device.

In certain aspects, the electrical current generating component may comprise a battery not contained within the housing.

Certain embodiments of the present disclosure may include a system for transcutaneously implanting a medical device, the system comprising a housing configured for placement on a skin surface of a host, an introducer configured to be at least partially positioned within the housing and having at least a portion engageable with at least a portion of a medical device, wherein the introducer is at least partially formed from a shape memory material, and a driving mechanism mechanically coupled to the introducer for moving the introducer relative to the housing to transition the introducer from a loaded configuration to an unloaded configuration, wherein said transition translates the medical device engaged with the introducer from a position within the housing to at least partially through the skin surface.

In certain aspects, the housing may comprise a compartment configured to physically retain the introducer in the loaded configuration.

Certain embodiments of the present disclosure may include an in vivo analyte monitoring system comprising a housing configured for placement on a skin surface of a host, a control unit housed within the housing, an in vivo analyte sensor having a proximal portion and a distal portion, wherein the proximal portion is operatively coupleable to the control unit, a sensor introducer at least partially positioned within the housing, wherein the introducer is at least partially comprised of a shape memory material and wherein a portion of the introducer is engageable with the sensor distal portion, and a transitioning component to transition the introducer from a first operative shape memory state to a second operative shape memory state, wherein said transitioning translates the sensor distal portion from a position within the housing to at least partially through the skin surface.

In certain aspects, the portion of the introducer engageable with the sensor distal portion may have a crosswise dimension substantially similar to that of the sensor distal portion.

In certain aspects, the portion of the introducer engageable with the sensor distal portion may have a crosswise dimension smaller than that of the sensor distal portion.

In certain aspects, the sensor distal portion and the portion of the introducer engageable with the sensor distal portion may have respective configurations which enable a nesting arrangement between them.

In certain aspects, the portion of the introducer engageable with the sensor distal portion may comprise a U-shaped configuration when in the first operative shape memory state.

In certain aspects, the introducer may comprise a distal tip configured to substantially atraumatically pierce the skin surface.

In certain aspects, the introducer may comprise at least one coupling member for securing the sensor distal portion to the introducer at least when the introducer is in the first operative memory state.

Certain embodiments of the present disclosure may include a transcutaneously implantable medical device comprising a flexible, elongated substrate having a distal tip configured to substantially atraumatically pierce the skin surface, wherein the substrate is formed from a non-conductive material, and at least one spine extending along a length of the substrate, wherein the at least one spine is formed from a shape memory material, and wherein the medical device is translatable from a first operative shape memory state to a second operative shape memory state.

In certain aspects, the first operative shape memory state may comprise a heat-unstable shape and the second operative shape memory state comprises a heat-stable shape.

In certain aspects, the first operative shape memory state may comprise a compressed configuration and the second operative shape memory state comprises an uncompressed configuration.

In certain aspects, the shape memory material may comprise one or more of nickel-titanium, copper-zinc-aluminum-nickel, copper-aluminum-nickel, and alloys of zinc, copper, gold and iron.

In certain aspects, the medical device may be an electrochemical sensor.

In certain aspects, the electrochemical sensor may comprise at least one electrode.

In certain aspects, at least one spine may function as the at least one electrode.

In certain aspects, the electrochemical sensor may be an analyte sensor.

In certain aspects, the analyte sensor may be a glucose sensor.

Certain embodiments of the present disclosure may include a method for transcutaneously implanting a medical device, at least a portion of which is flexible, the method comprising providing an introducer, wherein the introducer is at least partially formed from a shape memory material, engaging at least the flexible portion of the medical device with the introducer, wherein the engaged introducer and medical device are in a nested arrangement, and wherein the introducer is in a first operative shape memory state, positioning a skin-penetrating end of the introducer adjacent the skin surface, and transitioning the introducer from the first operative shape memory state to a second operative shape memory state, wherein the introducer penetrates through the skin surface and transcutaneously implants the flexible portion of the medical device.

In certain aspects, engaging the flexible portion of the medical device with the introducer in a nested arrangement may comprise cooling the introducer to a predefined temperature while the medical device is structurally aligned along a major axis of the introducer.

In certain aspects, transitioning the introducer from the first operative shape memory state to the second operative shape memory state may comprise applying a selected amount of electrical current to the introducer.

In certain aspects, engaging the flexible portion of the medical device with the introducer in a nested arrangement may comprise loading the introducer to a reduced profile while the medical device is structurally aligned along a major axis of the introducer and positioning the introducer and nested sensor in a confined space.

In certain aspects, transitioning the introducer from the first operative shape memory state to the second operative shape memory state may comprise releasing the introducer from the confined space.

In certain aspects, the confined space may be provided within a housing that is configured for placement on the skin surface.

Certain aspects may further comprise removing the introducer from the skin while leaving the medical device transcutaneously implanted.

In certain aspects, the removing the introducer from the skin while leaving the medical device transcutaneously implanted may comprise manually retracting the introducer from within the skin.

Certain aspects may further comprise maintaining the introducer within the skin along with the transcutaneously implanted medical device for the useful life of the medical device.

Certain aspects may further comprise simultaneously removing the introducer and the medical device from the skin subsequent to the expiration of the useful life of the medical device.

In certain aspects, the simultaneous removal of the introducer and the medical device from the skin may comprise manually retracting the introducer and the medical device.

In certain aspects, the simultaneous removal of the introducer and the medical device from the skin may comprise transitioning the introducer from the second operative shape memory state to the first operative shape memory state.

In certain aspects, the medical device may comprise an analyte sensor.

The preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A system for transcutaneously implanting a medical device, the system comprising:
    an introducer having at least a portion engageable with at least a portion of a medical device, wherein the introducer comprises a shape memory alloy having a predetermined activation temperature range,
        wherein the introducer, at a temperature below the predetermined activation temperature range, is in a first shape memory state configuration in which the introducer includes a first transition bend adjacent to a straight proximal portion of the introducer, and
        wherein the introducer, at a temperature above the predetermined activation temperature range, is in a second shape memory state configuration in which the introducer includes a second transition bend adjacent to a straight distal portion of the introducer; and
    an activating component to change the temperature of the introducer to transition the introducer from the first shape memory state configuration to the second shape memory state configuration, wherein said transition changes the shape of the introducer and translates the medical device engaged with the introducer from a position above the skin surface to a position at least partially through the skin surface;
    wherein said transition is driven by a martensitic-to-austenitic change of the shape memory alloy.

2. The system of claim 1 wherein the activating component comprises an electrical current generating component electrically coupled to the introducer to heat the introducer above the predetermined activation temperature range to cause the transition of the introducer from the first shape memory state configuration to the second shape memory state configuration.

3. The system of claim 1 further comprising a housing configured for releasable placement on a skin surface of a host using an adhesive, wherein the introducer is configured to be at least partially positioned within the housing when in the first shape memory state configuration.

4. The system of claim 3 wherein the housing comprises a compartment within which the introducer is configured to be at least partially contained when in the first shape memory state configuration.

5. The system of claim 1 wherein the shape memory alloy comprises one or more of nickel-titanium, copper-zinc-aluminum-nickel, copper-aluminum-nickel, and alloys of zinc, copper, gold and iron.

6. The system of claim 1 wherein the medical device is an analyte sensor and further wherein the portion of the introducer engageable with the medical device defines a major axis wherein, during the transition from the first shape memory state configuration to the second shape memory state configuration, a distal portion of the introducer changes shape along the major axis, while a proximal portion of the introducer remains fixed relative to the activating component.

7. The system of claim 1 wherein the introducer comprises at least one coupling member for securing the medical device to the introducer at least when in the first shape memory state configuration.

8. The system of claim 1 wherein the introducer, in the first shape memory state configuration, comprises a U-shaped distal portion that transitions at a bend to a straight proximal portion, and wherein the introducer, in the second shape memory state configuration, is L-shaped.

9. The system of claim 1, wherein the introducer includes an insulative layer to protect the user or medical device from heat or electrical damage.

10. The system of claim 1, wherein the location of the first transition bend along the length of the introducer differs from the location of the second transition bend.

11. The system of claim 1, wherein the location of the first transition bend along the length of the introducer coincides with the location of the second transition bend.

12. A method for transcutaneously implanting a medical device, at least a portion of which is flexible, the method comprising:
    engaging at least the flexible portion of the medical device with an introducer, wherein the engaged introducer and medical device are in a nested arrangement, and wherein the introducer comprises a shape memory alloy having a predetermined activation temperature range,
        wherein the introducer, at a temperature below the predetermined activation temperature range is in a first shape memory state configuration in which the introducer includes a first transition bend adjacent to a straight proximal portion of the introducer, and
        wherein the introducer, at a temperature above the predetermined activation temperature range is in a second shape memory state configuration in which the introducer includes a second transition bend adjacent to a straight distal portion of the introducer; and
    positioning a skin-penetrating end of the introducer adjacent the skin surface; and
    changing the temperature of the introducer to transition the introducer from the first shape memory state configuration to the second shape memory state configuration such that the introducer penetrates through the skin surface and transcutaneously implants the flexible portion of the medical device, and further wherein said transition changes the shape of the introducer, and is driven by a martensitic-to-austenitic change of the shape memory alloy.

13. The method of claim 12 wherein engaging the flexible portion of the medical device with the introducer in a nested arrangement comprises cooling the introducer below the predetermined activation temperature range while the medical device is structurally aligned along a major axis of the introducer, and wherein a distal portion of the introducer changes shape along the major axis, while a proximal portion of the introducer remains fixed relative to the activating component.

14. The method of claim 13 wherein transitioning the introducer from the first shape memory state configuration to the second shape memory state configuration comprises applying a selected amount of electrical current from an electrical current generating component electrically coupled to the introducer to heat the introducer above the predetermined activation temperature range.

15. The method of claim 12 further comprising removing the introducer from the skin while leaving the medical device transcutaneously implanted.

16. The method of claim 12 further comprising maintaining the introducer within the skin along with the transcutaneously implanted medical device for the useful life of the medical device.

17. The method of claim 16 further comprising simultaneously removing the introducer and the medical device from the skin subsequent to the expiration of the useful life of the medical device.

18. The method of claim 17 wherein the simultaneous removal of the introducer and the medical device from the skin comprises transitioning the introducer from the second shape memory state configuration to the first shape memory state configuration.

19. The method of claim 12 wherein the introducer, in the first shape memory state configuration, comprises a U-shaped distal portion that transitions at a bend to a straight proximal portion, and wherein the introducer, in the second shape memory state configuration, is L-shaped.

20. The method of claim 12, wherein the introducer includes an insulative layer to protect the user or medical device from heat or electrical damage.

* * * * *